United States Patent [19]

Huland et al.

[11] Patent Number: 5,780,012

[45] Date of Patent: *Jul. 14, 1998

[54] METHOD FOR REDUCING LUNG AFFLICTIONS BY INHALATION OF CYTOKINE SOLUTIONS

[76] Inventors: Edith Huland; Hartwig Huland, both of Barkenkoppel 8, D22391 Hamburg, Germany

[*] Notice: The portion of the term of this patent subsequent to Mar. 21, 2012, has been disclaimed.

[21] Appl. No.: 242,542

[22] Filed: May 13, 1994

Related U.S. Application Data

[63] Continuation-in-part of Ser. No. 717,824, Jun. 19, 1991, Pat. No. 5,399,341.

[30] Foreign Application Priority Data

Jun. 21, 1990 [EP] European Pat. Off. ............. 9011717

[51] Int. Cl.$^6$ .................................................. A61K 9/12
[52] U.S. Cl. ..................... 424/45; 424/450; 424/85.1; 424/85.2
[58] Field of Search .................. 424/43, 45, 450, 424/85.1, 85.2

[56] References Cited

U.S. PATENT DOCUMENTS

| | | | |
|---|---|---|---|
| 4,863,727 | 9/1989 | Zimmerman et al. | 424/85.2 |
| 5,011,678 | 4/1991 | Wang et al. | 424/45 |
| 5,037,644 | 8/1991 | Shaked et al. | 424/85 |
| 5,049,389 | 9/1991 | Radhakrishnan | 424/450 |
| 5,162,507 | 11/1992 | Wolfe et al. | 530/412 |

FOREIGN PATENT DOCUMENTS

| | | |
|---|---|---|
| 0 122 036 | 10/1984 | European Pat. Off. . |
| 0 173 990 | 3/1986 | European Pat. Off. . |
| 0 193 372 | 9/1986 | European Pat. Off. . |
| 0257956 | 2/1988 | European Pat. Off. . |
| 0 251 631 | 7/1988 | European Pat. Off. . |
| 0 333 523 | 9/1989 | European Pat. Off. . |
| 60-224616 | 11/1985 | Japan . |
| 62-207226 | 9/1987 | Japan . |
| 02124832 | 5/1990 | Japan . |

OTHER PUBLICATIONS

Lotze, M.T., et al. "Clinical Effects and Toxicity of Interleukin–2 in Patients With Cancer" Cancer 58: 2764, 1986.

Thompson, J.A., et al. "Recombinant Interleukin–2 Toxicity, Pharmacokinetics, and Immunomodulatory Effects in a Phase 1 Trial" Cancer Res. 47:4202, 1987.

West, W.H., et al. "Constant–Infusion Recombinant–Interleukin–2 in Adoptive Immunotherapy of Advanced Cancer" N.Engl.J.Med.: 898, 1987.

Lotze, M.T., et al. "High–Dose Recombinant Interleukin–2 in The Treatment of Patients with Disseminated Cancer" J.A.M.A. 256:3117, 1986.

Rosenberg, S.A., et al. "A Progress Report on the Treatment of 157 Patients with Advanced Cancer using Lymphokine–Activated Killer Cells and Interleukin–2 or High–Dose Interleukin–2 Alone" New Engl.J.Med. 316: 898, 1987.

Kucharz, E.J., et al. "Serum Inhibitors of Interleukin–2" Life Sci. 42: 1485, 1988.

Forni G., et al. "Tumor Immunotherapy by Local Injection of Interleukin–2 and Non–Reactive Lymphocytes", Prog. Exp.Tumor Res. 32: 187, 1988.

Gramatzki, M. et al. "Intralymphatic Interleukin–2 Treatment in Patients with Acquired Immunodeficiency Syndrome: Preliminary Experience in Three Case" Immunobiol.172:438,1986.

Bubenik, J. "Local immunotherapy of cancer with interleukin–2", Immunol. Let. 21: 267, 1989.

Lotze, M.T., et al. "Intraperitoneal Administration of Interleukin–2 in Patients with Cancer" Arch. Surg. 121: 1373, 1986.

Yasumoto, K., et al. "Induction of Lymphokine–activated Killer Cells by Intrapleural Instillations of Recombinant Interleukin–2 in Patients with Malignant Pleurisy Due to Lung Cancer" Cancer Res. 47: 2184, 1987.

Rosenberg, S.A. "Immunotherapy of Cancer by Systemic Admin. of Lymphoid Cells Plus Interleukin–2", J. Biol. Resp Mod 3: 501, 1984.

Mittelman, A., et al. "Treatment of Patients with Advanced Cancer Using Multiple Long–Term Cultured Lymphokine–Activated Killer (LAK) Cell Infusions and Recombinant Human Interleukin–2", J.Biol.Resp.Mod. 8: 468, 1989.

Rosenberg, S.A. "Lymphokine–Activated Killer Cells: A New Approach to Immunotherapy of Cancer" J.N.C.I. 75: 595, 1985.

Paciucci, P.A., et al. "Recombinant Interleukin–2 by Continuous Infusion and Adoptive Transfer of Recombinant Interleukin–2–Activated Cells in Patients with Advanced Cancer", J. Clin. Oncol. 7: 869, 1989.

Grimm, E.A., et al. "Lymphokine–Activated Killer Cell Phenomenon", J. Exp. Med. 155: 1823, 1982.

Rosenberg, S.A. "Observations on the Systemic Administration of Autologous Lymphokine–Activated Killer Cells and Recombinant Interleukin–2 To Patients with Metastatic Cancer", N.Engl.J.Med. 313: 1485, 1985.

(List continued on next page.)

*Primary Examiner*—Raj Bawa
*Attorney, Agent, or Firm*—Roberts & Mercanti,L.L.P.

[57] ABSTRACT

A method for administering to a patient having at least one affliction of infections, immunodeficiency syndromes, inflammatory diseases, autoimmune diseases, foreign body transplants, or requiring immuno-regulation of tumor diseases, which is present in the lungs. The method administers a non-systemic inhalation of an aerosol composition to the lungs effective to reduce the affliction. The aerosol composition is a solution of a cytokine and a pharmaceutically acceptable aqueous carrier solution. The aerosol composition is uniformly administered to the patient over a course of treatment of several months.

30 Claims, No Drawings

OTHER PUBLICATIONS

Belldegrun, A., "Lymphokines and activated cells in experimental and clinical immunotherapy" In: Immunotherapy of Urological Tumors (ed.deKernion JB), Churchill Livingston 1990.

Oliver, R.T.D. "The Clinical Potential of Interleulin-2" Br. J. Cancer 58.405–409, 1988.

Huland, Edith, et al, "Inhaled Interleukin-2 in Combination with low-dose systemic interleukin-2 and interferon-ã in patients with pulmonary metastatic renal-cell carcinoma: effectiveness and toxicity on mainly local treatment" J. Cancer Res. Clin. Oncol 120:221–228, 1994.

Van Zandwijk, et al, Aerosol Application Of Interferon-Alpha In The Treatment Of Bronchioalveolar Carcinoma, European Journal Of Cancer, vol. 26, No. 6, pp. 738–740, 1990.

Kinnula, V., et al., Effect Of Inhaled Natural Interferon-Alpha On Diffuse Bronchioalveolar Carcinoma, European Journal Of Cancer, vol. 26, No. 6, pp. 740–741, 1990.

Kinnula, V., et al, Pharmacokinetics And Toxicity Of Inhaled Human Interferon-Alpha In Patients With Lung Cancer, Journal Of Interferon Research, 9: pp. 419–423, 1989.

Flexman, JP, et al; In Vivo Boosting Of Lung Natural Killer And Lymphokine-Activated Killer Cell Activity By Interleukin-2: Comparison Of Systemic Intrapleural And Inhalation Routes Clin.Exp.Immunol, 82(1), pp. 151–156, 1990.

METHOD FOR REDUCING LUNG AFFLICTIONS BY INHALATION OF CYTOKINE SOLUTIONS

CROSS REFERENCE TO RELATED APPLICATION

This application is a continuation in part of application Ser. No. 07/717,824 filed Jun. 19, 1991 now U.S. Pat. No. 5,399,341 patented on Mar. 21, 1995 which is incorporated herein by reference.

BACKGROUND OF THE INVENTION

The influencing of the immune response by an immune enhancement agent can decisively determine the course of a disease. This is particularly the case with malignant tumors, infections caused by fungi, viruses, bacteria and parasites which cannot, or cannot adequately be given therapy, immuno-deficiency syndromes and by an immuno-suppression, e.g. in the case of foreign body transplants, autoimmune diseases or inflammatory diseases. Cytokines are able to stimulate cells of the immune system in such a way as to act in the immune process in an immuno-activating or immuno-suppressing manner.

Despite the excellent perspectives with respect to the treatment of therapy resistant and infectious diseases, considerable problems are encountered during the administration or application of such cytokines. The immuno-reaction provided by cytokines is difficult to control through the supply of exogenous cytokines. Only a rough immuno-response control is possible with the heretofore used systemic application processes (intravenous, intramuscular or subcutaneous cytokine administration). A further important disadvantage of the heretofore conventional systemic cytokine therapy is the extremely severe side effects, which lead to treatment only being possible with particularly good patients, who must in part be treated in intensive care units. Interleukin-2, interferon and the tumor necrosis factor have been particularly well tested in this connection. However, other cytokines are in experimental use.

Systemic side effects such as fever, shivers, nausea, vomiting, diarrhea, life-threatening effects on the cardiovascular system such as heterotonia (varying blood pressure), dysrhythmia and the much feared capillary leakage syndrome, i.e. water retention due to a vascular sealing loss, are accompanying phenomena of systemic immuno-enhancement by cytokines. These are discussed in: Lotze, M. T., et al, "Clinical Effects and Toxicity of Interleukin-2 in Patients With Cancer" *Cancer* 58: 2764, 1986; Thompson, J. A., et al, "Recombinant Interleukin-2 Toxicity, Pharmacokinetics, and Immunomodulatory Effects in a Phase 1 Trial" *Cancer Res.* 47: 4202, 1987; West, W. H., et al, "Constant-Infusion Recombinant-Interleukin-2 in Adoptive Immunotherapy of Advanced Cancer" *N.Engl.J.Med.:* 898, 1987; Lotze, M. T., et al, "High-Dose Recombinant Interleukin-2 in the Treatment of Patients with Disseminated Cancer" *J.A.M.A.* 256: 3117, 1986; Rosenberg, S. A., et al, "A Progress Report on the Treatment of 157 Patients with Advanced Cancer using Lymphokine-Activated Killer Cells and Interleukin-2 or High-Dose Interleukin-2 Alone" *New Engl.J.Med.* 316: 898, 1987; and Lotze, M. T., et al, "High-Dose Recombinant Interleukin-2 in the Treatment of Patients With Disseminated Cancer" *J.A.M.A.* 256: 3117, 1986.

In addition, systemic therapy is made more difficult by the fact that cytokines are rapidly eliminated from the blood. For example, interleukin-2 has a half-life in the blood of 13 minutes. A further problem is that the blood contains powerful cytokine inhibitors. (See Kucharz, E. J., et al. "Serum Inhibitors of Interleukin-2" *Life Sci.* 42: 1485, 1988).

Local administration of cytokines leads to far fewer side effects. In this regard see Forni G., et al. "Tumor Immunotherapy by Local Injection of Interleukin-2 and Non-Reactive Lymphocytes", *Prog. ExD.Tumor Res.* 32: 187, 1988; Gramatzki, M. et al, "Intralymphatic Interleukin-2 Treatment in Patients with Acquired Immunodeficiency Syndrome: Preliminary Experience in Three Cases" *Immunobiol.* 172: 438, 1986; Bubenik. J. "Local immunotherapy of cancer with interleukin-2", *Immunol. Let.* 21: 267, 1989; Lotze, M. T., et al. "Intraperitoneal Administration of Interleukin-2 in Patients with Cancer" *Arch. Surg.* 121: 1373, 1986; Yasumoto, K., et al. "Induction of Lymphokine-activated Killer Cells by Intrapleural Instillations of Recombinant Interleukin-2 in Patients with Malignant Pleurisy Due to Lung Cancer" *Cancer Res.* 47: 2184, 1987. However at present no use is made thereof, because there is almost always a systemic disease at hand, such as metastasized tumor, generalized immune deficiency (AIDS) and autoimmune diseases and adequate immuno-stimulation is not brought about through a short term, local application. The technically complicated, expensive and patient-stressing method of adoptive infusion of immune cells has been employed as a way out. In this regard see Rosenberg, S. A. "Immunotherapy of Cancer by Systemic Administration of Lymphoid Cells Plus Interleukin-2", *J. Biol. Resp Mod* 3: 501, 1984; Mittelman, A., et al, "Treatment of Patients with Advanced Cancer Using Multiple Long-Term Cultured Lymphokine-Activated Killer (LAK) Cell Infusions and Recombinant Human Interleukin-2", *J.Biol.Resp.Mod.* 8: 468, 1989; Rosenberg, S. A. "Lymphokine-Activated Killer Cells: A New Approach to Immunotherapy of Cancer", *J.N.C.I.* 75: 595, 1985; Paciucci, P. A., et al, "Recombinant Interleukin-2 by Continuous Infusion and Adoptive Transfer of Recombinant Interleukin-2-Activated Cells in Patients with Advanced Cancer", *J. Clin. Oncol.* 7: 869, 1989; Grimm, E. A., et al, "Lymphokine-Activated Killer Cell Phenomenon", *J. Exp. Med.* 155: 1823, 1982; Rosenberg, S. A. "Observations on the Systemic Administration of Autologous Lymphokine-Activated Killer Cells and Recombinant Interleukin-2 To Patients with Metastatic Cancer", *N.Engl.J.Med.* 313: 1485, 1985; Belldegrun, A., "Lymphokines and activated cells in experimental and clinical immunotherapy" In: *Immunotherapy of Urological Tumors* (ed. deKernion J B), Churchill-Livingston1990.

Endogenic immune cells have been taken from the patient (cf. FIG. 24.1 in Belldegrun, ibid.), which are either cells from the blood, which are non-specifically stimulatable, or immune cells are directly obtained from the tumor, i.e. from the diseased or affected area, which are specifically stimulatable against antigens. These immune cells are then mixed with corresponding cytokines in vitro, i.e. in the test tube and are replaced after successful stimulation. This involves considerable effort and expenditure, above-average quantities of equipment and specially trained staff (cf.FIG. 24.2 in Belldegrun, ibid.). The taking of these immune cells involves an infection risk for the patient. The re-infusion can also represent an infection source for the patient (hepatitis transmission has been reported). As the cells are firstly taken from the patient and then stimulated in vitro, in the case of repeated therapy cycles, intervals occur between the individual therapies, which is not desired with such diseases. For these and other reasons, the aforementioned application cannot be used as a long-term process lasting months or even years. However, a long-term application is the prerequisite for effective immunotherapy.

The problem which the invention seeks to solve is to develop a cytokine application, which can continuously extend over a long period, i.e. months to years, which has few side effects and which still has a powerful systemic action. Application must be simple and rapidly performable for the patient, without requiring equipment or processes which are complicated with regard to technology and personnel. According to the invention this problem is surprisingly solved by the use of cytokine-containing aerosols for inhalative application and immuno-activation or continuous immuno-regulation in tumor diseases or the use of cytokine-containing substances for producing an aerosol medicinal preparation for inhalative application and immuno-activation or continuous immuno-regulation in tumor diseases, and by daily doses between approximately 2 and 5×100,000 U BRMP, 2 and 5×200,000 U BRMP, 5×300,000 U BRMP, particularly 5×100,000 U BRMP and 5×200,000 U BRMP.

The inhalative application of medicaments is not novel per se. However, this has hitherto involved the use of other medicaments and with completely different aims, e.g. asthma patients or allergic persons e.g. inhale substances during an acute pulmonary disease, e.g. for expectoration purposes. In the case of AIDS patients, antibiotics are applied by inhalation, to avoid local infection risks. However, the inventive concept of obtaining a systemic action, in that the large local surface of approximately 100m$^2$ of the lung is utilized in order to activate immune cells reachable on this surface, and to make the same available to the circulatory system, satisfies a longstanding need for achieving very high tumor regression throughout the body by simple application or administration.

Equally novel and characteristic for the inventive use of cytokine-containing aerosols is the advantageous use over many months and daily application for many days. This combination induces an optimum, continuous immuno-stimulation, which cannot be achieved as efficiently and without side effects in any other way. The effectiveness can not only be measured through the regression of metastases, but also on the cytotoxicity of the stimulated cells.

The analysis of the inventively obtained cytotoxicity shows a clearly increased tumor toxicity of the immune cells present in the blood, and also in the phase when the ambulatory patient only receives an inhalative cytokine application and not a systemic application. This high effectiveness and extremely good compatibility could not have been foreseen. Interleukin-2 systemically brings about a considerable liquid incorporation, so that intravenously treated patients have a considerable risk of a pulmonary edema developing. The inventive application form by aerosol inhalation has not as yet revealed this side effect in patients. A dosage increase has only led to the occurrence of moderate systemic effects (fever, blood pressure reduction, etc.).

Cytokines have been available in unpurified form for decades. For roughly ten years gene-technologically produced and well characterized cytokines have been available. Although the application form of cytokines has been intensely discussed in smaller and also larger research, cytokine aerosol application has not been as yet considered anywhere in the world. There are two main reasons for this. Firstly, such an impressive systemic immuno-stimulation could not be expected through this local application form and secondly, significant and much more dangerous side effects were expected, namely pulmonary edema, and the induction of lung allergies, etc.

A further possible reason might be that no data was available giving information on the stability and penetrability of cytokines in the form of an aerosol application. Aerosol production equipment has long been known. However, cytokine aerosol application has never been considered. The inventive inhalative application form with cytokine-containing aerosols has already proved very effective within the scope of a pilot study in the case of patients with incurable carcinomas. Advantageously the cytokine decisive for immuno-activation, i.e. interleukin-2, is applied to the patient by inhalation as an aerosol several times daily. The hitherto well accepted doses may vary between 2 and 5×100,000 U BRMP and experience exists with dosage increases up to 5×500,000 U BRMP/day. Two patients have been treated with this inhalative application for six months and have surprisingly revealed no side effects in the lungs.

SUMMARY OF THE INVENTION

The invention provides a method for treating a patient having at least one affliction selected from infections, immunodeficiency syndromes, inflammatory diseases, autoimmune diseases, foreign body transplants, or requiring immuno regulation of tumor diseases. The method comprises causing such a patient to inhale an amount of a nebulized aerosol composition effective to reduce the affliction. The aerosol composition consists essentially of a solution of at least one cytokine, at least one serum protein, and a sufficient amount of a pharmaceutically acceptable aqueous carrier solution therefor to form a homogeneous solution. The carrier contains at least one component selected from the group consisting of a pharmaceutically acceptable salt, buffer and sugar.

The invention also provides for a method for treating patients having such afflictions by causing such a patient to inhale an aerosol composition which comprises only at least one cytokine and a pharmaceutically acceptable carrier which is an aqueous solution of a salt, buffer or sugar.

DETAILED DESCRIPTION OF THE PREFERRED EMBODIMENT

The method of this invention provides for a method of treating patients by the inhalation of a homogeneous aqueous solution containing a cytokine; a serum protein; and an aqueous carrier solution containing at a pharmaceutically acceptable salt, buffer or sugar.

The cytokines useful for this invention include natural cytokines, i.e. those produced by purification, or artificially produced cytokines such as those made by recombinant production, including gene engineering and protein engineering. Cytokines useful for this invention include interleukins such as interleukin-1, interleukin-2, interleukin-3, interleukin-4, interleukin-5, interleukin-6, interleukin-7, interleukin-8, interleukin-9, interleukin-10, interleukin-11, interleukin-12; interferon alpha, interferon beta, interferon gamma, as well as sub groups such as interferon alpha 2 b among others. Cytokines may include an acidic fibroblast growth factor, basic fibroblast growth factor, epidermal growth factor, erythropoietin, granulocyte colony stimulating factor, granulocyte-macrophage colony stimulating factor, colony stimulating factor, macrophage colony stimulating factor, insulin growth factor, stem cell factor, leukemia inhibitory factor, nerve growth factor, platelet derived growth factor, transforming growth factor alpha, tumor necrosis factor beta, melanoma growth stimulatory activity, neutrophil activating protein, platelet factor, macrophage inflammatory protein, peptide regulatory factors, prostaglandin, platelet activating factor, plasminogen activator inhibitor, thrombomodulin, tissue plasminogen activator and thromboplastin. In addition, receptors of these proteins and antagonists to these proteins are contemplated by the invention. The most preferred cytokine is an interleukin, and most preferably interleukin-2, recombinant interleukin-2 and glycosylated interleukin-2. Most recombinant proteins are produced to have a structure to closely resemble the natural protein and to imitate the biological function of their natural counterpart. The better this is achieved, the more it can be expected that the recombinant protein will behave like the natural protein in biological activity and pharmacokinetics. Recombinant proteins have the advantage that they can be produced less expensively, because costly purification procedures are not required and sometimes this is the best or only way to produce enough substance for extensive testing and pharmacologic use. For inhalation purposes the solutions allow recovery of the cytokine and do not affect the biological activity or the function of the target cell for the cytokine. In the use of IL-2 one type of target cell for that purpose is lymphocytes. In the preferred embodiment, the cytokine is present in an amount of from about 0.001 mg/ml to about 0.9 mg/ml of the aerosol composition.

The aerosol composition also contains a serum protein. The addition of 0.1% protein or more in the solution for nebulization, preferably human serum albumin, optimizes the biological effect of the cytokines. It also leads to a better recovery after in vitro nebulization. Other useful serum proteins non-exclusively include immunoglobulin, serum protein extract, plasma protein extract and immunoglobulin M containing polyvalent immunoglobulin. Useful immunoglobulins non-exclusively include immunoglobulin IgG-Anti-Hepatitisvirus, IgG-Anti-Cytomegalovirus and IgG-Anti-HIV. Preferably the serum protein is present in an amount of from about 0.1 to about 20% by weight of the aerosol composition. Concentrations between 0.1–20% were tested and a dose dependency found in correlation to recovery of the cytokine after nebulization. Addition of the serum protein can be omitted completely if the cytokine content of the solution is at least≧0.5 mg/ml. This represents a very high cytokine concentration and can substitute for the addition of human serum albumin and allow recovery and biological activity of the drug, however this is of lesser practical importance because this is an extremely expensive method.

The aerosol composition used for the method contains an aqueous carrier solution of a pharmaceutically acceptable salt, buffer or sugar. Non-exclusive examples of these include dextrose, fructose, sodium chloride, monobasic sodium phosphate, dibasic sodium phosphate, sodium bicarbonate, ringer's solution, lactated ringer's solution, sodium lactate, and aqua ad injectabilia or sterile water for injection. The pharmaceutically acceptable salt, buffer or sugar is preferably present in an amount of from about 0.001 mg/ml to about 0.020 g/ml of the aerosol composition.

The aerosol composition may optionally contain an additive such as amino acids, acetates, malates, lactates, aspartates, phosphates, sorbitol, xylit and mannitol. When it is present, the additive is present in an amount of from about 0.001 mg/ml to about 0.020 g/ml of the aerosol composition. The aerosol composition may optionally further comprise a pharmaceutically acceptable aqueous solution of a detergent provided it is used in an amount below the critical micelle concentration. Non-limiting examples of such detergents include anionic, cationic, non-ionic and amphoteric surfactants which do not produce any mammalian toxicity. These are well known in the art and may include such as detergents as sodium dodecyl sulfate; polyoxyethylene (20) sorbitol monooleate, polyoxyethylene (9–10) nonylphenol, polyethyleneglycol; and propane sulfonate in an amount of from about 0.01 mg/ml to about 0.5 mg/ml. It is important for this invention that if a detergent is included that the amount of detergent be below the critical micelle concentration. This is because it has been determined that detergents kill cells in cell cultures. The critical micelle concentration is that concentration at which monomeric detergent molecules join to form micelles. The aerosol composition may also optionally contain a small amount of a base such as sodium hydroxide or an acid such as hydrochloric acid to bring the composition into the usual physiological pH range of from about 4 to about 9 or more usually from about 6.5 to about 7.5. It is also important for this invention that the composition of this invention does not include any other ingredients such as liposomes or phospholipids. The presence of liposomes, phospholipids or a detergent above the critical micelle concentration would defeat the operation of the invention since they cannot be inhaled without toxic side effects. A particularly preferred aerosol composition comprises an aqueous solution of human serum albumen, sodium chloride, a phosphate buffer and a cytokine which is interleukin-2, recombinant interleukin-2 or glycosylated interleukin-2. A particularly preferred aerosol composition comprises an aqueous solution of human serum, dextrose, mannitol, dibasic sodium phosphate, monobasic sodium phosphate, and sodium dodecyl sulfate and recombinant interleukin-2.

Cytokine administration takes place with an atomizer, which produces very small droplets and therefore ensures an optimum distribution over the lung surface. In addition, a pre-atomization with a buffer albumin solution is advantageous, to avoid adhesion of the cytokine to the surface of the tube system. This application form could even be used during a short, clinical preliminary period in ambulatory manner and consequently offers a possibility of long-term therapy. Existing data shows that this application form is not only patient-friendly, i.e. very compatible in that it has virtually no side effects for a dosage of approximately 5×200.000 U BRMP, but is also extremely effective.

In one preferred embodiment as an aerosol, the medicament can have the following composition: Interleukin-2 100.000 U BRMP/ml in 0.1% (wt/vol) human serum albumin, 0.01M phosphate buffer with 0.15M NaCl, pH 7.4. As a function of the desired application quantity, a higher interleukin-2 concentration per ml can be chosen. The buffer solution can also be replaced by a physiological common salt solution, without any limitations being feared. Alternatively comparable buffer solutions can be used. The pre-atomization solution is not applied to the patient and instead merely serves to block protein binding points in the tube system, so that here interleukin-2 is not non-specifically bound and lost for patient therapy.

The following non-limiting examples serve to illustrate the invention.

The clinical effects are discussed hereinafter relative to two patients.

EXAMPLE 1

A first patient has a metastasized kidney tumor. Initial diagnosis took place in October 1989 as tumor nephrectomy. At this time there was considerable metastasization of the tumor in the lungs with functional impairment of the lung in the form of dyspnea. This was followed by systemic interferon-alpha therapy under which the tumor progressed in measurable form. Systemic interleukin-2 therapy began in December 1989. With unchanged severe metastasization in January 1990, there was increasing weight loss (from 80 to 54 kg) and increasing dyspnea (breathlessness even when speaking). This was supplemented by daily multiple interleukin inhalation as described above. There was a clear tumor regression as shown by X-rays of the thorax. During therapy the weight increased, up to now by 12 kg, to 66 kg. Clearly increased fitness of the patient and in particular no further dyspnea is observed.

EXAMPLE 2

A second patient had a metastasized renal cell carcinoma. The initial diagnosis revealing tumor nephrectomy took place in October 1988, metastases not being detected then. A computer tomograph first revealed local lymph node metastases, as well as enlarged lymph nodes in the mediastinum and several lung metastases in September 1989. Interferon-alpha therapy started in November 1989 and was accompanied by systemic interleukin-2 therapy due to further tumor progression. There was no reduction in the tumor metastases and therefore it was decided to give inhalative cytokine application with interleukin-2. Within 3 weeks there was regression of the lung metastase and clear reduction of the mediastinal and regional lymph node metastases during the following 3 months. Therapy has lasted 6 months up to now.

Both treated patients are still in a phase of continual tumor regression, so that they are on the best path to full remission. The improvement to the quality of life, the weight increase and the disappearance of dyspnea in patient 1 are largely due to the inhalative application and not or only to a limited extent to the intravenous application. It is to be expected that other cytokines, besides interleukin-2, will be equally effective.

EXAMPLE 3

To a solution containing per ml:

| Interleukin-2 (Cetus) | 3.6 × 10⁶ IU |
| --- | --- |
| Mannitol | 10 mg |
| Sodium dodecyl sulfate | 0.036 mg |
| Monobasic sodium phosphate | 0.034 mg |
| Dibasic sodium phosphate | 0.178 mg |
| dextrose 5% | to make 1.0 ml | were added either 0.5% or 2.0% or 5% of human serum albumin. After in vitro nebulization of these two solutions the average percent recovery of the cytokine was determined. With 0.5% HSA the average recovery of 45 nebulizations was 17%, with 2.0% HSA the average recovery of 45 nebulizations was 28%, with 5% the average recovery was 36%. Instead of human serum albumin a 0.1–10% serum protein solution (produced as a virus safe extract of fresh human serum and containing not only human serum albumin but also other serum proteins like immunoglobulins) can be used also, however the product is much more expensive and there is an at least theoretical risk of infection in natural blood products.

EXAMPLE 4

Use of solutions in patients with pulmonary metastases

The following compositions are successfully used in 2 ml single dose inhalations five times a day.

| Contents per ml: | Solution 1 | Solution 2 |
|---|---|---|
| Interleukin-2 | 1.8 Million IU (0.11 mg) | 3.6 Million IU (0.22 mg) |
| Mannitol | 5 mg | 10 mg additive |
| Sodium dodecyl sulfate | 0.018 mg | 0.036 mg detergent |
| Monobasic sodium phosphate | 0.017 mg | 0.034 mg buffer |
| Dibasic sodium phosphate | 0.089 mg | 0.178 mg buffer |
| Human serum albumin | 5% | 5% protein |
| dextrose 5% | to make 1 ml | to make 1 ml |

The specific type of interleukin-2 was non-glycosylated recombinant interleukin-2 (Proleukin/Cetus).

Three patients have been treated with five inhalations per day continuously for 6, 5 and 4 months respectively. Patients started with solution 1 for 6 weeks and then continued treatment with solution 2. Treatment was tolerated well, one patient had a 25% reduction of pulmonary metastatic disease (defined as minor response) lasting for 7 months. Two patients were stabilized during their treatment times. Discontinuation of the treatment lead after a delay of about 4–8 weeks to regrowth of the tumor. After restart of the treatment growth of pulmonary metastases was stopped again. This approach was successful in controlling the growth of pulmonary metastases. Treatment had a very low toxicity allowing one to treat patients in reduced general health. One patient had an insulin dependent diabetes for more than ten years, one patient had a history of cardiac problems. Treatment with the same amount of cytokine given systemically either intravenously or subcutaneously would not be possible in any of these patients and even not in patients with good general health for such a long time. The addition of very low dose systemic cytokine treatment (10% of the total inhaled dose) was acceptable with no increase in toxicity of the inhalative approach.

EXAMPLE 5

In vitro nebulization of solutions for inhalators treatment

Solutions containing the following substance have been nebulized and tested for biological activity of drug successfully with good recovery of cytokine:

| | |
|---|---|
| G-CSF (r-metHuG-CSF) (Commercial name Neupogen) | 0.030 mg/ml |
| human serum albumin | 0.2% |
| NaOH | 0.0035 mg |
| mannitol | 5 mg |
| polysorbate 80 | 0.0004% |
| acetate | 0.059 mg |
| Water for injection or dextrose 5% | to make 1 ml |

EXAMPLE 6

In vitro nebulization of solutions for inhalators treatment

Solutions containing the following substance have been nebulized and tested for biological activity of drug successfully with good recovery of cytokine:

| | |
|---|---|
| GM-CSF (rh GM-CSF) (Commercial name Leucomax) | 0.200 mg/ml |
| human serum albumin | 0.1% |
| sodium phosphate (dibasic) | 1.3 mg/ml |
| mannitol | 2.5 mg/ml |
| polyethylene glycol 3350 | 0.05 mg/ml |
| citric acid (anhydrous) | 0.14 mg/ml |
| Water for injection or dextrose 5% | to make 1 ml |

EXAMPLE 7

Comparative data of systemic and inhalative immunotherapy with identical solutions and identical doses of IL-2. IL-2 manufacturer Biotest. Daily dose IL-2 $1\times10^6$ U BRMP. Solution contains 0.01M phosphate buffer
0.15M NaCl
0.1% (wt/vol) human serum albumin

| TOXICITY OF SYSTEMIC (I.V.) ROUTE | TOXICITY OF INHALATIVE ROUTE |
| --- | --- |
| Inpatient treatment | Outpatient treatment, patients can continue to do their jobs. |
| Systemic toxicity (fever > 40° C. toxicity, hypotension, dyspnea, tachycardia, diarrhea, vomiting and other). | No significant systemic no fever, no hypotension, no dyspnea, no tachycardia, no diarrhea, no vomiting. Cough and hoarse voice in 20-60% of the patients. |
| Treatment of selected patients only (performance status according to ECOG 0 or Karnofsky 90%-100%). | No patient selection required. Everybody able to inhale, can perform treatment. Toxicity is not the limiting factor. |
| Regular co-medication necessary. | No regular co-medication necessary. |
| Despite co-medication toxicity up to grade WHO III. Substitution of intravenous fluids necessary. | Maximum grade I WHO toxicity (if at all). Neither oral nor intravenous substitution of fluids necessary. |
| Maximum tolerated continuous treatment duration was 4 days. | Maximum tolerated treatment so far 3 years. Treatment is still continued. |
| Long-term toxicity not evaluable because not possible to perform treatment for more than a few days. | No long-term toxicity (normal pulmonary function, no fibrosis, no chronic inflammation, no autoimmune disease). |
| Dose increase would require intensive care (toxicity is dose dependent). | Dose increase possible without significant toxicity to $2.5 \times 10^6$ U BRMP per day. |

EXAMPLE 8

Comparative data of systemic and inhalative immunotherapy with identical solutions and identical doses of IL-2. IL-2 manufacturer IL-2 (Cetus). Daily dose $36\times10^6$ IU Solution contains 5% Dextrose and 5% human serum albumin in buffered solution.

| TOXICITY OF SYSTEMIC (I.V.) ROUTE | TOXICITY OF INHALATIVE ROUTE |
| --- | --- |
| Inpatient treatment | Outpatient treatment, patients can continue to do their jobs. |
| Systemic toxicity (fever > 40° C. toxicity, hypotension, dyspnea, tachycardia, diarrhea, vomiting and other). | No significant systemic no fever, no hypotension, no dyspnea, no tachycardia, no diarrhea, no vomiting. Cough and hoarse voice in 40-80% of the patients (dose dependent). |
| Treatment of selected patients only (performance status according to ECOG 0 or Karnofsky 90%-100%). | No patient selection required. Everybody able to inhale, can perform treatment. Toxicity is not the limiting factor. |
| Regular co-medication necessary. | No regular co-medication necessary. |
| Despite co-medication toxicity up to grade WHO III. Substitution of oral and in some patients of intravenous fluids necessary. | Maximum grade I WHO toxicity (if at all). Neither oral nor intravenous substitution of fluids necessary. |
| Maximum tolerated continuous treatment duration was 3 days. | Maximum tolerated treatment so far 10 months. No evidence so far for long term toxicity. |
| Long-term toxicity not evaluable because not possible to perform treatment for more than a few days. | Up to 10 months no induction of fibrosis or autoimmune disease. (No longer experience available) |
| Dose increase would require intensive care (toxicity is dose dependent). | Dose increase not tested. |

These examples compare systemic immunotherapies (intravenous via a large venous catheter centrally or peripherally and subcutaneous injection) by IL-2 application versus inhalative IL-2 application in comparable aqueous solutions. It can be seen that identical doses and identical solutions differ completely in their toxicity if an inhalative application is used. Systemic application induces significant toxicity with little difference in the different systemic routes (intravenous via peripheral or central catheter, intraperitoneal and subcutaneous). Patients had to be treated inpatient, no regular performance of daily activities is possible for the patient, co-medication has to be given continuously and in spite of that considerable toxicity occurred limiting the treatment time to days and even with breaks in between to a maximum of weeks. Not all patients rather, only patients selected to a good general performance status could be considered for treatment.

During inhalation of identical doses and compositions of IL-2, however, no significant systemic toxicity was observed and only minor local side effects like cough and hoarse voice. All patients who were able to perform their daily routine before treatment were still able to continue to do so during inhalative IL-2 treatment. Treatment was effective and tumor remissions and stabilizations were induced. The best tumor remissions so far have been achieved with the solution containing Interleukin-2 in buffer, protein as human serum albumin and low concentrations of salt. Up to this time it seemed clear to those skilled in the art that a high toxicity would occur using such solutions for inhalation and that additional additives (like lipids or liposomes) of unknown toxicity would at least be required to hopefully reduce IL-2 toxicity and maintain its effects. This new experience that a cytokine could be used in buffered solutions with only a small amount of human serum albumin as an inhalant and remain effective without toxicity is completely unexpected. IL-2 as many other biological response modifiers is eliminated quickly from the body, blocked by substances in serum, tumors and tissues and biological activity can be impaired by bacterial inflammation, viral infection and local tumor disease. The lining of the alveoli with surfactant factor and mucus can be considered to be an additional problem for the safe transfer of cytokine activity. The requirement of protective additives like liposomes seemed clearly necessary if IL-2 as an inhalant would be useful at all. In view of our comparative results and in view of the data concerning systemic immunotherapy the good relation of toxicity to effect in this specific inhalative immunotherapeutic approach is completely unexpected.

EXAMPLE 9

Cell Cultures are treated with IL-2 stimulated lymphocytes with solutions with detergents above the critical micelle concentration and compared to treatment with similar solutions without detergents. Each solution contains 0.9% (9 mg/ml) of sodium chloride, 20 U/ml of IL-2 and the indicated additional ingredient.

| Lymphocytes cells/ml | Detergent | Concentration | % of Vital cells after 30 minutes incubation |
|---|---|---|---|
| $10^5$ | Polyoxyethylene monolaurate | 60 mg/ml (6%) | 0 |
| $10^5$ | Polyoxyethylene monolaurate | 30 mg/ml (3%) | 0 |
| $10^5$ | Polyoxyethylene monolaurate | 15 mg/ml (1.5%) | 0 |
| $10^5$ | Polyoxyethylene monolaurate | 9 mg/ml (0.9) | 0 |
| $10^6$ | Polyoxyethylene monolaurate | 60 mg/ml (6%) | 0 |
| $10^6$ | Polyoxyethylene monolaurate | 30 mg/ml (3%) | 0 |
| $10^6$ | Polyoxyethylene monolaurate | 15 mg/ml (1.5%) | 0 |
| $10^6$ | Polyoxyethylene monolaurate | 9 mg/ml (0.9) | 0 |
| $10^5$ | No Detergent But 0.1% human serum albumin | | 95% |
| $10^5$ | No Detergent But 0.1% human serum albumin | | 95% |
| $10^5$ | No Detergent But 0.1% human serum albumin | | 100% |
| $10^5$ | No Detergent But 0.1% human serum albumin | | 100% |
| $10^6$ | No Detergent But 0.1% human serum albumin | | 100% |
| $10^6$ | No Detergent But 0.1% human serum albumin | | 95% |
| $10^6$ | No Detergent But 0.1% human serum albumin | | 95% |
| $10^6$ | No Detergent But 0.1% human serum albumin | | 95% |

These data show that the use of detergent above the critical micelle concentration is toxic to lymphocytes after 30 minutes of incubation. This means that the main target cell for immuno-modulation is damaged severely by the addition of detergent above the critical micelle concentration. A solution that kills cells in vitro would not be useful for inhalation purposes. In contrast, solutions without the detergent above the critical micelle concentration but with human serum albumin according to this invention are essentially non-toxic under these conditions.

EXAMPLE 10

The following are useful solutions for natural and recombinant cytokines in inhalatory use in patients. Examples for cytokine: natural IL-2, recombinant glycosylated IL-2 and recombinant non-glycosylated IL-2. As protein human serum albumin or serum protein solution (Biseko) was used.

| | |
|---|---|
| Solution 1 | |
| Natural Interleukin-2 | 100,000 U BRMP/ml |
| human serum albumin | 0.1% (wt./vol.) |
| phosphate buffer (0.01M with 0.15M NaCl, pH 7.4) | |
| Solution 2 | |
| Natural Interleukin-2 | 200,000 U BRMP/ml |
| human serum albumin | 0.1% (wt./vol.) |
| phosphate buffer (0.01M with 0.15M NaCl, pH 7.4) | |
| Solution 3 | |
| Recombinant glycosylated Interleukin-2 | 166,000 IU/ml |
| human serum albumin | 0.5% (wt./vol.) |
| phosphate buffer (0.01M with 0.15M NaCl, pH 7.4) | |
| Solution 4 | |
| Recombinant glycosylated Interleukin-2 | 500,000 IU/ml |
| human serum albumin | 0.5% (wt./vol.) |
| phosphate buffer (0.01M with 0.15M NaCl, pH 7.4) | |
| Solution 5 | |
| Recombinant glycosylated Interleukin-2 | 500,000 IU/ml |
| human serum albumin | 0.5% (wt./vol.) |
| phosphate buffer (0.01M with 0.15M NaCl, pH 7.4) | |
| Solution 6 | |
| Recombinant non-glycosylated Interleukin-2 | 1.8 million IU/ml |
| mannitol | 5 mg/ml |
| sodium dodecyl sulfate | 0.0164 mg/ml |
| human serum albumin | 0.1% (wt./vol.) |
| phosphate buffer (0.01M with 0.15M NaCl, pH 7.4) | |
| Solution 7 | |
| Recombinant non-glycosylated Interleukin-2 | 3.6 Million IU (0.22 mg) |
| Mannitol | 10 mg additive |
| Sodium dodecyl sulfate | 0.036 mg detergent |
| Monobasic sodium phosphate | 0.034 mg buffer |
| Dibasic sodium phosphate | 0.178 mg buffer |
| Human serum albumin | 2% |
| dextrose 5% | to make 1 ml |
| Solution 8 | |
| Recombinant non-glycosylated Interleukin-2 | 1.8 Million IU (0.11 mg) |
| Mannitol | 5 mg |
| Sodium dodecyl sulfate | 0.018 mg |
| Monobasic sodium phosphate | 0.017 mg |
| Dibasic sodium phosphate | 0.089 mg |
| Human serum albumin | 2% |
| dextrose 5% | to make 1 ml |

An analysis of the foregoing solutions shows the following content.

| Interleukin-2 | Na (mM) | K (mM) | Ca (mM) | Cl (mM) | Protein (g/L) | Phosphate (mM) |
|---|---|---|---|---|---|---|
| 1. Natural IL-2 | 180 | 0.2 | 0.04 | 154 | 1 | 10.0 |
| 2. Natural IL-2 | 150 | 0.2 | 0.20 | 130 | 1 | 8.6 |
| 3. Rec.gly IL-2 | 228 | 6.8 | 0.08 | 148 | 5 | 10.0 |
| 4. Rec.gly IL-2 | 219 | 6.7 | 1.10 | 143 | 5 | 40 |
| 5. Rec.gly IL-2 | 225 | 0.3 | 0.12 | 142 | 5 | 38.5 |
| 6. Rec. IL-2* | 220 | 0.3 | 0.22 | 140 | 1 | 38.5 |

-continued

| Interleukin-2 | Na (mM) | K (mM) | Ca (mM) | Cl (mM) | Protein (g/L) | Phosphate (mM) |
|---|---|---|---|---|---|---|
| 7. Rec. IL-2* | 18 | 0.1 | 0.14 | 15 | 21 | 0.03 |
| 8. Rec. IL-2* | 21 | 0.1 | 0.06 | 16 | 22 | 1 |

*contains sodium dodecyl sulfate in concentration 0.0164 mg/ml, 0.033 mg/ml (50–100 times below critical micelle concentration) and mannitol 5–10 mg/ml in dextrose 5% or water.

This readily controllable application form for cytokines can also be used for other diseases, which can be influenced by cytokines, inter alia immunodeficiency syndromes, therapy-resistant infections, foreign body transplants, autoimmune diseases and therapy-resistant, and inflammatory diseases.

What is claimed is:

1. A method for administering to a patient having at least one affliction selected from the group consisting of an infection, immunodeficiency syndrome, inflammatory disease, autoimmune disease, foreign body transplant, and tumor disease requiring immuno-regulation, which affliction is present in the lungs, which method consists essentially of administering to the lungs a non-systemic application of an amount of a nebulized aerosol composition effective to reduce the affliction, which aerosol composition consists essentially of a solution of I. at least one cytokine; and II. a sufficient amount of at least one pharmaceutically acceptable aqueous carrier solution therefor to form a homogeneous solution, said carrier solution selected from the group consisting of sterilized water, a pharmaceutically acceptable salt solution, a buffer solution and a sugar solution, wherein the aerosol composition is uniformly administered to the patient for a plurality of months.

2. The method of claim 1 wherein the cytokine is an interleukin.

3. The method of claim 1 wherein the cytokine is selected from the group consisting of interleukin-2, recombinant interleukin-2 and glycosylated interleukin-2.

4. A method for administering to a patient having at least one affliction selected from the group consisting of an infection, immunodeficiency syndrome, inflammatory disease, autoimmune disease, foreign body transplant, and tumor disease requiring immuno-regulation, which affliction is present in the lungs, which method consists esssentially of administering to the lungs a non-systemic application of an amount of a nebulized aerosol composition effective to reduce the affliction, which aerosol composition consists essentially of a solution of I. at least one cytokine; and II. a sufficient amount of at least one pharmaceutically acceptable aqueous carrier solution therefor to form a homogeneous solution, said carrier solution selected from the group consisting of sterilized water, a pharmaceutically acceptable salt solution, a buffer solution and a sugar solution, and III. a serum protein selected from the group consisting of, human serum albumen, immunoglobulin, and plasma protein;

wherein the aerosol composition is uniformly administered to the patient for a plurality of months.

5. The method of claim 4 wherein the immunoglobulin is selected from the group consisting of immunoglobulin M, containing polyvalent immunoglobulin, immunoglobulin IgG-Anti-Hepatitis virus, IgG-Anti-Cytomegalovirus and IgG-Anti-HIV.

6. The method of claim 1 wherein the pharmaceutically acceptable aqueous carrier solution consists essentially of at least one component selected from the group consisting of dextrose, fructose, sodium chloride, monobasic sodium phosphate, dibasic sodium phosphate, sodium bicarbonate, Ringer's solution, lactated Ringer's solution, sodium lactate, and sterilized water.

7. The method of claim 1 wherein the pharmaceutically acceptable aqueous carrier solution consists essentially of water and at least one pharmaceutically acceptable additive selected from the group consisting of acetates, malates, lactates, aspartates, phosphates, sorbitol, xylitol and mannitol.

8. The method of claim 1 wherein the pharmaceutically acceptable aqueous carrier solution consists essentially of water, at least one pharmaceutically acceptable detergent in an amount below the critical micelle concentration, and at least one component selected from the group consisting of a pharmaceutically acceptable salt, a buffer and a sugar.

9. The method of claim 8 wherein the detergent is selected from the group consisting of sodium dodecyl sulfate; polyoxyethylene 20 sorbitol monooleate, polyoxyethylene 9–10 nonylphenol, polyethyleneglycol; and propane sulfonate.

10. The method of claim 1 wherein the cytokine is present in an amount of from about 0.001 mg/ml to about 0.9 mg/ml of the aerosol composition.

11. The method of claim 4 wherein the serum protein is present in an amount of from about 0.1 to about 20% by weight of the aerosol composition.

12. The method of claim 1 wherein the pharmaceutically acceptable salt, buffer or sugar is present in an amount of from about 0.001 mg/ml to about 0.020 g/ml of the aerosol composition.

13. The method of claim 7 wherein the pharmaceutically acceptable additive is present in an amount of from about 0.001 mg/ml to about 0.020 g/ml of the aerosol composition.

14. The method of claim 8 wherein the pharmaceutically acceptable detergent is present in an amount of from about 0.01 mg/ml to about 0.5 mg/ml.

15. The method of claim 4 wherein the aerosol composition consists essentially of an aqueous solution of human serum albumen, sodium chloride, a phosphate buffer and a cytokine selected from the group consisting of interleukin-2, recombinant interleukin-2 and glycosylated interleukin-2.

16. The method of claim 4 wherein the aerosol composition consists essentially of an aqueous solution of at least one cytokine, human serum, dextrose, mannitol, dibasic sodium phosphate, monobasic sodium phosphate, and sodium dodecyl sulfate.

17. The method of claim 16 wherein the cytokine is recombinant interleukin-2.

18. A method for administering to patients having at least one affliction selected from the group consisting of an infection, immunodeficiency syndrome, inflammatory disease, autoimmune disease, foreign body transplant, and tumor disease requiring immuno regulation, which affliction is present in the lungs, which method consists essentially of administering to the lungs a non-systemic application of an aerosol composition, in an amount effective to reduce the affliction, which aerosol composition consists essentially of a solution of I. a cytokine and II. a pharmaceutically acceptable carrier therefor wherein the pharmaceutically acceptable carrier is human serum albumen and a component selected from the group consisting of one or more of a pharmaceutically acceptable salt solution, and a pharmaceutically acceptable buffer.

19. The method of claim 18 wherein the cytokine is interleukin-2.

20. The method of claim 1 wherein the aerosol composition is administered to the patient a plurality of times daily.

21. The method of claim 18 wherein the composition is administered to the patient by means of an atomizer producing atomized droplets of the composition.

22. The method of claim 18 wherein the composition is administered to the patient in daily doses in the range of from about 2 to about 5 times 100,000 U BRMP.

23. The method of claim 18 wherein the composition is administered to the patient in daily doses in the range of from about 2 times 100,000 U BRMP to about 5 times 500,000 U BRMP.

24. The method of claim 18 wherein the pharmaceutically acceptable carrier is human serum albumen and a component selected from the group consisting of one or more of a sodium chloride solution, and a phosphate buffer solution.

25. The method of claim 18 wherein the pharmaceutically acceptable carrier is a mixture of human serum albumen, a sodium chloride solution and a phosphate buffer solution.

26. The method of claim 25 wherein the pharmaceutically acceptable aqueous carrier solution consists essentially of at least one component selected from the group consisting of dextrose, fructose, sodium chloride, monobasic sodium phosphate, dibasic sodium phosphate, sodium bicarbonate, Ringer's solution, lactated Ringer's solution, sodium lactate, and sterilized water.

27. A method for administering to a patient having at least one affliction selected from the group consisting of an infection, immunodeficiency syndrome, inflammatory disease, autoimmune disease, foreign body transplant, and tumor disease requiring immuno regulation, which affliction is present in the lungs, which method consists essentially of (a) administering to the lungs a non-systemic application of an amount of a nebulized aerosol composition effective to reduce the affliction, which aerosol composition consists essentially of a solution of
  I. at least one cytokine; and
  II. a sufficient amount of at least one pharmaceutically acceptable aqueous carrier solution therefor to form a homogeneous solution, said carrier containing at least one component selected from the group consisting of sterilized water, a pharmaceutically acceptable salt solution, a buffer solution and a sugar solution; and b) administering a systemic application of an amount of a cytokine, and wherein the composition is uniformly administered to the patient for a plurality of months.

28. A method for administering to a patient having at least one affliction selected from the group consisting of an infection, immunodeficiency syndrome, inflammatory disease, autoimmune disease, foreign body transplant, and tumor disease requiring immuno regulation, which affliction is present in the lungs, which method consists essentially of (a) administering to the lungs a non-systemic application of an amount of a nebulized aerosol composition effective to reduce the affliction, which aerosol composition consists essentially of a solution of
  I. at least one cytokine; and
  II. a sufficient amount of at least one pharmaceutically acceptable aqueous carrier solution therefor to form a homogeneous solution, said carrier solution selected from the group consisting of sterilized water, a pharmaceutically acceptable salt solution, a buffer solution and a sugar solution; and
  III. a serum protein selected from the group consisting of, human serum albumen, immunoglobulin and plasma proteins;

b) administering a systemic application of an amount of a cytokine, and wherein the composition is uniformly administered to the patient for a plurality of months.

29. The method of claim 28 wherein the immunoglobulin is selected from the group consisting of immunoglobulin M, containing polyvalent immunoglobulin, immunoglobulin IgG-Anti-Hepatitis virus, IgG-Anti-Cytomegalovirus and IgG-Anti-HIV.

30. The method of claim 27 wherein the aerosol composition is administered to the patient a plurality of times daily.

* * * * *